(12) United States Patent
Ippen et al.

(10) Patent No.: US 6,511,985 B1
(45) Date of Patent: Jan. 28, 2003

(54) COMBINATION OF CERIVASTATIN AND FIBRATES

(75) Inventors: Joachim Ippen, Leverkusen (DE); Ulrike Schopen, Cary, NC (US); Reiner Ziegler, Wuppertal (DE); Fritz Schückler, Bergisch Gladbach (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/868,444

(22) PCT Filed: Dec. 6, 1999

(86) PCT No.: PCT/EP99/09524

§ 371 (c)(1),
(2), (4) Date: Jun. 18, 2001

(87) PCT Pub. No.: WO00/37078

PCT Pub. Date: Jun. 29, 2000

(30) Foreign Application Priority Data

Dec. 18, 1998 (DE) .......................................... 198 58 789

(51) Int. Cl.⁷ .................. A61K 31/4418; A61K 31/216; A61K 31/195
(52) U.S. Cl. .................. 514/277; 514/543; 514/563
(58) Field of Search ................. 514/277, 543, 514/563

(56) References Cited

U.S. PATENT DOCUMENTS

| 4,895,726 A | 1/1990 | Curtet et al. | 424/456 |
| 5,177,080 A | 1/1993 | Angerbauer et al. | 514/277 |
| 5,827,536 A | 10/1998 | Laruelle | 424/451 |

FOREIGN PATENT DOCUMENTS

| EP | 0276807 | 8/1988 |
| EP | 0455042 | 11/1991 |
| WO | 8201649 | 3/1982 |

OTHER PUBLICATIONS

Deslypere, J. P., "The Role of HMG–CoA Reductase Inhibitors in the Treatment of Hyperlipidemia: A Review of Fluvastatin", Current Ther. Res., 56(2): 111–128 (1995).

Feussner, G.; Eichinger, M.; and Ziegler, R., "The Influence of Simvastatin Alone or in Combination with Gemfibrozil on Plasma Lipids and Lipoproteins in Patients with Type III Hyperlipoproteinemia", Clin. Investig., 70(11): 1027–1035 (1992).

Rader, D. J.; and Haffner, S. M., "Role of Fibrates in the Management of Hypertriblyceidemia", Am. J. Cardio., 83(9B): 30F–35F (May 1999).

Shviro, I.; and Leitersdorf, R., "Targeted Prevention of Coronary Artery Disease: Pharmacological Considerations in Multimodality Treatment", Cardiology, 87(6): 469–475 (1996).

*Primary Examiner*—Phyllis G. Spivack
(74) *Attorney, Agent, or Firm*—Susan M. Pellegrino

(57) ABSTRACT

The present invention relates to the combination of the 3-hydroxy-3-methylglutaryl-coenzyme A inhibitor (HMG-CoA inhibitor) cerivastatin with fibrates and its use in the prophylaxis and treatment of disorders of lipid metabolism.

12 Claims, No Drawings

COMBINATION OF CERIVASTATIN AND FIBRATES

The present invention relates to the combination of the 3-hydroxy-3-methylglutaryl-coenzyme A inhibitor (HMG-CoA inhibitor) cerivastatin with fibrates and its use in the prophylaxis and treatment of disturbances and diseases of lipid metabolism and of disorders caused thereby.

EP-A-0 276 807 describes the combination of HMG-CoA reductase inhibitors having a hexahydronaphthalene parent structure with gemfibrozil and the use of this combination for the regulation of the lipid and cholesterol level in the blood serum.

EP-A-0 455 042 discloses the combination of pravistatin with a fibrate and its use for the treatment of dyslipidaemia. Reference is expressly made to the discussion of the further prior art in this document and in the abovementioned EP-A-0 276 807.

The combination of the HMG-CoA reductase inhibitor cerivastatin with fibrates has not been described until now. It has now been found that the combination of cerivastatin with fibrates has advantageous properties, in particular with respect to action and tolerability.

The present invention therefore relates to the combination of cerivastatin with a fibrate.

Cerivastatin is the INN for (+)-[3-R,5S,(E)]-7-[4-(4-fluorophenyl)-2,6-diisopropyl-5-methoxymethylpyrid-3-yl]-3,5-dihydroxyhept-6-enecarboxylic acid. In the context of the present invention, the term cerivastatin is also intended to include the esters, the lactone and, in particular, pharmaceutically tolerable salts. Cerivastatin is particularly preferably employed in the form of its sodium salt ("cerivastatin sodium").

Fibrates in the context of this invention are understood as meaning derivatives and analogues of clofibric acid. In the context of the invention, fenofibrate, 1-methylethyl 2-[4-(4-chlorobenzoyl)phenoxy]-2-methylpropanoate, and bezafibrate, 2-[4-[2-[(4-chlorobenzoyl)amino]-ethyl]phenoxy]-2-methyl-propanoic acid, are preferred. Fenofibrate is particularly preferred.

According to a preferred embodiment, the combination according to the invention comprises no further pharmaceutical active compounds apart from cerivastatin and fibrate, in particular fenofibrates.

The combination of cerivastatin with fibrates according to the invention proves to be surprisingly advantageous in the treatment of disturbances of lipid metabolism. An example which may be mentioned is dyslipidaemias, such as occur in diabetics but also in patients who do not suffer from diabetes. When using the combinations according to the invention, an additive effect which is not to be expected is observed in the action, for example in the lowering of the LDL (low density lipoprotein) level. The amounts of cerivastatin and fibrate employed can thus be lowered in comparison with monotherapy.

The combinations according to the invention are furthermore distinguished by a surprisingly good tolerability, although in the literature numerous indications of disadvantageous side effects such as, for example, rhabdomyolyses, are to be found. Thus severe cases of rhabdomyolysis have been described for patients who were given the combination of lovastatin with gemfibrozil or nicotinic acid (Physician's Desk Reference, 52$^{nd}$ Ed., 1998, p. 1695).

The combinations according to the invention are therefore suitable for the prophylaxis and treatment of disturbances of the lipid levels in the blood and of diseases connected therewith. The combinations according to the invention are therefore preferably employed for the treatment of dyslipidaemia.

"Dyslipidaemia" is intended here as meaning a mixed hyperlipidaemia, i.e. a disease state with an increased cholesterol level (LDL and total cholesterol) and increased triglyceride level. Dyslipidaemias, however, can also occur with a normal total cholesterol level or LDL cholesterol level and/or a normal triglyceride level. In this case, dyslipidaemia is understood as meaning a shift of the spectrum of the lipid particles to particularly atherogenic lipid particles. Examples of such atherogenic particles which may be mentioned are the small dense particles (a subfraction of the LDL particles) or the chylomicron remnants. The combinations according to the invention are suitable for the treatment of both variants of dyslipidaemia.

An increased cholesterol level is referred to in this connection in the case of values of over 200 mg/dl for total cholesterol or over 130 mg/dl for LDL cholesterol, an increased triglyceride level is present at values of over 150 mg/dl.

The combinations according to the invention are particularly also suitable for the treatment of dyslipidaemias in diabetics.

On account of their action on the serum lipid levels, the combinations according to the invention are furthermore particularly suitable for the prophylaxis and treatment of atherosclerosis.

The combinations according to the invention are preferably employed in human medicine, but are also suitable for veterinary medicine, in particular for the treatment of mammals.

The administration of the combinations according to the invention can be carried out parenterally or preferably orally.

The active compounds can be converted in a known manner into the customary formulations, it being possible for these to be liquid or solid formulations. Examples are tablets, coated tablets, pills, capsules, granules, aerosols, syrups, emulsions, suspensions and juices.

As cerivastatin is active in very low doses, very different types of formulation variants can be produced. Thus on the one hand there is the possibility of formulating the individual components separately. In this case, the two individual components do not necessarily have to be taken at the same time, but on the contrary taking of cerivastatin and fibrate at different times can be advantageous. In the case of a separate administration of this type, it suggests itself to combine the formulations of the two individual components, for example tablets or capsules, at the same time next to one another in a suitable primary pack.

Further formulation variants which are also suitable for the combinations according to the invention are fixed combinations. "Fixed combination" is intended here as meaning those pharmaceutical forms in which the two components are present together in a fixed quantitative ratio. Fixed combinations of this type can be produced, for example, as peroral solutions, but preferably they are solid oral pharmaceutical preparations, e.g. capsules or tablets. In the context of this invention, the fixed combinations are preferred.

The combinations of cerivastatin with fibrates according to the invention are administered up to 3×daily, those combinations are preferred which allow administration 1×daily.

The formulations contain 0.025 mg to 4 mg of cerivastatin sodium, 0.2 mg to 1.6 mg are preferred, and 2 mg to 2000 mg of a fibrate, preferably 10 mg to 500 mg. Fibrates within the meaning of the invention are in particular fenofibrate and bezafibrate.

To achieve efficacious results, the combinations according to the invention are in general administered orally in daily doses of approximately 1 to 60 µg/kg of cerivastatin and 0.1 to 100 mg/kg of fibrate; in the case of parenteral administration the dose is approximately 0.5 to 30 µg/kg of cerivastatin and 0.05 to 50 mg/kg of fibrate based on the respective body weight.

If appropriate, it may be necessary to depart from the amounts mentioned, namely depending on the body weight or on the type of administration route, on the individual behaviour towards the medicaments, the manner of their formulation and the time or interval at which administration takes place. Thus, in some cases it may be adequate to manage with less than the abovementioned minimum amount, while in other cases the upper limit mentioned has to be exceeded. In the case of the administration of relatively large amounts, it may be advisable to divide these into a number of individual doses over the course of the day.

In this connection, it has furthermore proved advantageous that fenofibrate can optionally also be administered—on account of particular pharmaceutical process optimizations (see, for example, EP 0757911 A1)—in doses of 200mg and less, which are comparatively low for fibrates.

The two active compounds cerivastatin and fenofibrate are accordingly particularly suited to be formulated in a fixed combination in the form of a solid peroral administration form. It is generally known that the reliability of taking (compliance) in the case of patients is dependent to a decisive extent on the factors number of administration forms per time of taking and size and weight of the (solid peroral) pharmaceutical form. The number of the different medicaments to be taken separately should therefore be as low as possible (advantage of a fixed combination), and the size and the weight of a solid peroral administration form should be as small as possible in order to make taking for the patients as pleasant as possible. No other fixed combination of statins with fibrates known at present can be administered—with full therapeutic potency—at a lower dose than that of cerivastatin with fenofibrate. Fixed combinations in the form of solid peroral pharmaceutical formulations of minimal size and minimal weight can thus be produced. The fixed combinations of cerivastatin and fenofibrate according to the invention accordingly offer the highest possible patient compliance and thereby improve the safety and reliability of a therapy decisively.

For pharmacological reasons, the administration of cerivastatin is preferably carried out in the evening. Fibrates, even fenofibrate or bezafibrate, are often given in the morning. As a rule, clinical studies with these preparations are carried out according to the dosage scheme mentioned, but other dosage schemes are possible. By means of combination of the two preparations and modification of the composition or of the functionality, the release of active compound can be controlled. For example, by means of the delayed release of active compound (retardation) of one component the abovementioned decoupling in terms of time of the onset of action can be realized. One form of the retardation of fenofibrate is described, for example, in WO 82/01649.

The solid peroral administration forms mentioned here are prepared by the general standard processes. Ingredients are those which are pharmaceutically accepted and physiologically innocuous, for example, as fillers: cellulose derivatives (e.g. micro-crystalline cellulose), sugars (e.g. lactose), sugar alcohols (e.g. marmitol, sorbitol), inorganic fillers (e.g. calcium phosphates), binders (e.g. polyvinylpyrrolidone, gelatine, starch and cellulose derivatives), and all other excipients which are needed for the production of pharmaceutical formulations with the desired properties, e.g. lubricants (magnesium stearate), e.g. disintegrants (e.g. crosslinked polyvinyl-pyrrolidone, sodium carboxymethylcellulose), e.g. wetting agents (e.g. sodium lauryl sulphate), e.g. retarding agents (e.g. cellulose derivatives, polyacrylic acid derivatives), e.g. stabilizers, e.g. flavourings, e.g. colour pigments.

Liquid formulations are also prepared according to a standard method using pharmaceutically customary excipients and contain the active compound or the two active compounds either in dissolved or suspended form. Typical administration volumes of these pharmaceutical preparations are 1 to 10 ml. Examples of excipients in these liquid formulations are: solvents (e.g. water, alcohol, natural and synthetic oils, e.g. medium-chain triglycerides), solubilizers (e.g. glycerol, glycol derivatives), wetting agents (e.g. polysorbate, sodium lauryl sulphate), and further excipients which are needed for the production of pharmaceutical preparations with the desired properties, e.g. viscosity-increasing agents, e.g. pH corrigents, e.g. sweeteners and flavourings, e.g. antioxidants, e.g. stabilizers, e.g. preservatives.

The main constituents of the shells of capsule formulations are, for example, gelatine or hydroxypropylmethylcellulose.

Pharmaceutical excipients, as are familiar to the person skilled in the art, are also described, for example, in the following handbook: "Handbook of Pharmaceutical Excipients", Wade, A. & Weller, P. J., American Pharmaceutical Association, Washington, 2nd edition 1994.

EXAMPLES

Example 1

Separate Formulation

Cerivastatin tablets having an active compound content of 0.4 mg per tablet and the following composition were prepared as described below.

| Component | [mg/tablet] |
| --- | --- |
| Cerivastatin sodium | 0.40 |
| Mannitol | 83.65 |
| Sodium hydroxide | 0.10 |
| Povidone (polyvinylpyrrolidone) | 1.80 |
| Crospovidone (crosslinked polyvinylpyrrolidone) | 2.70 |
| Magnesium stearate | 1.35 |

The process is a conventional moist granulation (typical batch sizes are 5 kg–120 kg), in which mannitol is introduced into the apparatus as a powder base and granulated with a granulating fluid, comprising cerivastatin sodium, sodium hydroxide, polyvinylpyrrolidone and water. After drying, the granules are sieved (0.8–1.25 mm), mixed after addition of magnesium stearate and crospovidone (5–15 min), tabletted (90 mg/tablet) and optionally coated with a photoprotective lacquer. By means of variation of the contents of active compound and mannitol in the composition, strengths of action of the tablets of 0.025 mg to 4 mg are possible.

Fenofibrate tablets are prepared according to a standard method.

Cerivastatin tablets and fenofibrate tablets are employed together for the treatment of the lipid metabolic disorders described above as a combination in a suitable primary pack.

Example 2

Separate Formulation

Cerivastatin tablets according to Example 1 are employed as a combination in a suitable primary pack with capsule formulations, comprising granules, powder mixtures or pellets (delayed-release formulation) containing fenofibrate, in some cases in special preparations or preparation forms (according to composition and preparation, as described, for example, in EP 0 330 532 A1 or in French Patent No. 2 494 112).

Example 3
Fixed Combination

Cerivastatin granules (according to Example 1) are mixed with fenofibrate granules, powder mixture or pellets in appropriate quantitative ratios and tabletted; the tablets are then coated with a photoprotective lacquer.

Example 4
Fixed Combination

Cerivastatin granules according to Example 1 are dispensed together with fenofibrate granules, powder mixtures or pellets in appropriate quantitative ratios into capsules (made of hard gelatine or cellulose derivatives). This is carried out either on suitable capsule filling machines having 2 metering units or on simplified machines after prior combination and homogenization of the two components.

Example 5
Fixed Combination

Cerivastatin tablets are prepared according to Example 1 and dispensed into capsules together with a fenofibrate formulation of the appropriate dose, powder mixture, granules or pellets.

Example 6
Fixed Combination (Capsules)

Cerivastatin sodium and fenofibrate are mixed in a joint process, if appropriate with addition of further constituents, and optionally granulated. These mixtures or granules are then dispensed into capsules.

Example 7
Fixed Combination (Tablets)

The mixtures or granules according to Example 6 are tabletted, if appropriate with addition of further excipients; the tablets are then coated with a photoprotective lacquer.

Example 8
Fixed Combination (Pellets)

Pellets of uniform size and loading are prepared from mixtures according to Example 6 in special processes by rounding off and are either dispensed into capsules or tabletted, if appropriate with addition of further excipients.

Example 9
Fixed Combination (Pellets)

Active compound-free pellets (nonpareils) are loaded with a solution which contains cerivastatin sodium and further excipients. These pellets are combined with fenofibrate pellets and dispensed into capsules.

Example 10
Fixed Combination

The pellets according to Example 9 are processed to give tablets, if appropriate with addition of further excipients.

Example 11
Fixed Combination (Liquid)

A liquid formulation of cerivastatin and fenofibrate (according to the description in EP 0 757 91 1 A1) are mixed in appropriate amounts and made available as a solution for administration.

Example 12
Fixed Combination

A formulation of the two substances according to Example 11 is dispensed into soft gelatine capsules having a specific administration volume.

Example 13

Formulations according to Examples 1 to 12, where bezafibrate—instead of fenofibrate—is combined with cerivastatin in a suitable dose of up to 500 mg.

Example 14
Action on the Lipid Levels

In the course of a diet-controlled clinical double-blind study, patients were treated once daily in the evening with 0.3 mg of cerivastatin in the form of tablets and with 200 mg of fenofibrate (capsules/micronized).

The results after 16 weeks are summarized in the following table for treatment with fenofibrate or cerivastatin on its own and with the combination. The percentage change in each case is indicated, based on the starting value.

|  | Cholesterol (total) | LDL cholesterol | HDL cholesterol | Tri-glycerides |
|---|---|---|---|---|
| Cerivastatin 0.3 mg | −20.7% | −29.3% | +6.5% | −10.8% |
| Fenofibrate 200 mg | −16.2% | −21.8% | +13.0% | −32.2% |
| Cerivastatin 0.3 mg + Fenofibrate 200 mg | −30.4% | −41.3% | +13.0% | −38.7% |

What is claimed is:

1. A combination consisting of cerivastatin with a fibrate.
2. The combination according to claim 1, characterized in that the fibrate is fenofibrate or bezafibrate.
3. The combination according to claim 1 of cerivastatin with fenofibrate.
4. The combination according to claim 1, characterized in that it comprises no other pharmaceutical active compounds apart from cerivastatin and the fibrate.
5. The combination according to claim 1, characterized in that cerivastatin is contained in an amount from 0.025 mg to 4 mg.
6. The combination according to claim 1, characterized in that the fibrate is contained in an amount from 2 mg to 2000 mg.
7. A medicament, comprising the combination according to claim 1, and a pharmaceutical auxiliary.
8. The medicament according to claim 7, characterized in that it is formulated as a fixed combination.
9. The medicament according to claim 8, characterized in that the fibrate is formulated such that the action of the fibrate occurs in a controlled manner.
10. The medicament of claim 9, wherein said fibrate is fenofibrate.
11. A process for the production of medicaments according to claim 7, characterized in that the active compounds are mixed with suitable pharmaceutical excipients and the mixture is converted into a suitable formulation.
12. A method of treating or preventing disorders of lipid metabolism, comprising administering to a mammal an effective amount of the combination of claim 1.

* * * * *